(12) United States Patent
Baratto et al.

(10) Patent No.: US 12,163,875 B2
(45) Date of Patent: Dec. 10, 2024

(54) REMOTE AIR COLLECTION

(71) Applicant: The Boeing Company, Chicago, IL (US)

(72) Inventors: Joseph M. Baratto, Seattle, WA (US); Ryan B. Wilson, Bainbridge Island, WA (US)

(73) Assignee: The Boeing Company, Chicago, IL (US)

( * ) Notice: Subject to any disclaimer, the term of this patent is extended or adjusted under 35 U.S.C. 154(b) by 184 days.

(21) Appl. No.: 17/647,212

(22) Filed: Jan. 6, 2022

(65) Prior Publication Data
US 2022/0228955 A1 Jul. 21, 2022

Related U.S. Application Data

(60) Provisional application No. 63/140,105, filed on Jan. 21, 2021.

(51) Int. Cl.
*G01N 1/22* (2006.01)
*G01N 27/416* (2006.01)
(Continued)

(52) U.S. Cl.
CPC ....... *G01N 1/2226* (2013.01); *G01N 33/0075* (2013.01); *G01N 27/416* (2013.01); *G01N 30/7206* (2013.01)

(58) Field of Classification Search
CPC .......... G01N 1/02; G01N 1/22; G01N 1/2226; G01N 1/2273; G01N 1/24; G01N 1/26; G01N 2001/002; G01N 33/0075
See application file for complete search history.

(56) References Cited

U.S. PATENT DOCUMENTS 3,122,158 A * 2/1964 Grunsky ............... G01F 15/185
137/271
5,050,425 A 9/1991 Robbins
(Continued)

FOREIGN PATENT DOCUMENTS

WO 9942814 8/1999

OTHER PUBLICATIONS

European Patent Office Extended Search Report, dated Jun. 21, 2022, regarding Application No. EP21208419.8, 9 pages.
(Continued)

*Primary Examiner* — Kristina M Deherrera
*Assistant Examiner* — Fatemeh Esfandiari Nia
(74) *Attorney, Agent, or Firm* — Yee & Associates, P.C.

(57) ABSTRACT

An air monitoring system with a controller in a computer system that operates to control a pump system to move air from a collection port for a cavity as diverted air to a tube connected to the collection port, move the diverted air into an input port of an air interface connected to the tube, through a chamber in the air interface, and out of a pump port of the air interface without increasing a pressure of the diverted air greater than a pressure level for a gas analyzer system to analyze an air sample collected from the diverted air. The controller operates to control the gas analyzer system connected to a sampling port in the air interface by a probe to obtain the air sample from the diverted air moving through the air interface and analyze the air sample to determine a set of components in the air sample.

21 Claims, 10 Drawing Sheets

(51) Int. Cl.
    *G01N 30/72*         (2006.01)
    *G01N 33/00*         (2006.01)

(56)                 References Cited

U.S. PATENT DOCUMENTS

| | | | |
|---|---|---|---|
| 9,091,618 B1* | 7/2015 | Baratto | G01N 1/2226 |
| 2006/0272393 A1 | 12/2006 | Jenkins | |
| 2008/0281528 A1* | 11/2008 | Relle, Jr. | G01N 1/2273 |
| | | | 702/50 |
| 2013/0232976 A1* | 9/2013 | Tillery | F17D 3/00 |
| | | | 60/734 |
| 2014/0238107 A1* | 8/2014 | Chou | G01N 33/0075 |
| | | | 73/23.36 |
| 2018/0128802 A1* | 5/2018 | Al Azri | G01N 33/497 |
| 2021/0190647 A1* | 6/2021 | Bounouar | G01N 33/0011 |

OTHER PUBLICATIONS

European Patent Office Communication, dated Jun. 13, 2024, regarding Application No. 21208419.8, 5 pages.

\* cited by examiner

REMOTE AIR COLLECTION

CROSS-REFERENCE TO RELATED APPLICATION

This application claims the benefit of U.S. Provisional Patent Application Ser. No. 63/140,105, filed Jan. 21, 2021, and entitled "Remote Air Collection;" which is incorporated herein by reference in its entirety.

BACKGROUND INFORMATION

1. Field

The present disclosure relates generally to aircraft and, in particular, to collecting air samples from remote locations in the aircraft.

2. Background

Air can be sampled in an aircraft for a number of different reasons. For example, air sampling can be used in designing and testing aircraft. For example, with respect to moisture control in an aircraft, airflow can occur in cavities between insulation blankets and the skin on a fuselage of the aircraft. This airflow can occur in locations where frost, condensation, or both can form during flight of the aircraft. The airflow can cause undesired movement of moisture. For example, the condensation of moisture in an undesired location can cause an entry of water into a passenger cabin. The aircraft can be designed to control airflow such that the moisture is moved to drainage collectors to reduce the moisture that may result in water causing undesired conditions in the aircraft Air sampling can be used as part of the design and testing process to detect the airflow. This air sampling includes injecting a gas into the cavities of the aircraft where moisture control is desired. For example, a gas, such as xenon, can be injected into a location in cavities between the insulation blankets and the skin.

Air samples can be collected from different locations in the cavities and analyzed to determine whether the injected gas is present at those locations. Detection of the gas in these different locations in the cavities is used to analyze the airflow. This analysis can be made to determine whether adequate moisture control is present or to make changes in the design of the aircraft to obtain desired moisture control in these cavities.

As another example, sampling of air can be performed to determine air quality in an aircraft. Samples of air can be collected from various locations such as in a passenger cabin, cargo areas, or other locations within the aircraft. These air samples can be analyzed to determine the air quality during operation of aircraft.

For example, the air samples can be collected during the flight of the aircraft to identify air quality issues such as odors or the presence of undesired gases during the flight of the aircraft. Real-time monitoring can be performed to identify air quality issues in a manner that enables resolution of these air quality issues.

For example, identification of an odor from melting polystyrene foam or a burnt smell from overheating food in a microwave can be detected through sampling and analyzing air samples from different locations in real-time. In this example, the detection of an odor in a galley can enable a flight attendant or other cabin crew member to resolve the issue.

Collection of the air samples from different locations in the aircraft can be performed by moving portable gas analysis to different locations or by installing a network of conduits through which gas samples can be obtained for analysis. These types of sampling techniques can be more difficult to use or implement than desired. For example, currently, air samples to be collected and tested must be within 3 feet of portable testing apparatus such as the gas chromatography mass spectrometer (GS-MS) apparatus.

Therefore, it would be desirable to have a method and apparatus that take into account at least some of the issues discussed above, as well as other possible issues. For example, it would be desirable to have a method and apparatus that overcome a technical problem with collecting air samples from different locations in an aircraft without having to be in close proximity to the air sample.

SUMMARY

An embodiment of the present disclosure provides an air monitoring system comprising an air interface, a first seal mechanism connected to the input port, and a second seal mechanism connected to the sampling port. The air interface comprises a chamber in a body, the chamber in fluid communication with an input port, a sampling port, and a pump port. The first seal mechanism forms a first airtight seal at the input port when a tube is connected to the input port. The second seal mechanism forms a second airtight seal at the sampling port when a probe for a gas analyzer system is inserted into the sampling port. A diverted air moves into the input port, through the chamber, and out of the pump port without increasing a pressure of the diverted air greater than a pressure level for the gas analyzer system to analyze an air sample from the diverted air when the diverted air is drawn through the chamber and out of the pump port. The probe obtains the air sample from the diverted air moving through the chamber.

Another embodiment of the present disclosure provides an air monitoring system comprising a computer system and a controller in the computer system. The controller operates to control a pump system to move air from a collection port for a cavity as diverted air to a tube connected to the collection port, move the diverted air into an input port of an air interface connected to the tube, through a chamber of the air interface, and out of a pump port of the air interface without increasing a pressure of the diverted air greater than a pressure level for a gas analyzer system to analyze an air sample collected from the diverted air. The collection port is at a location in the cavity in a platform and an airtight seal is present between the tube and the input port. The controller controls the gas analyzer system connected to a sampling port in the air interface by a probe to obtain the air sample from the diverted air moving through the air interface and analyze the air sample to determine a set of components in the air sample.

Yet another embodiment of the present disclosure provides a method for monitoring air. Air is moved from a collection port connected to a tube as diverted air. The diverted air is moved from the tube through an input port in an air interface, through a chamber of the air interface, and out of a pump port in the air interface without increasing a pressure of the diverted air greater than a pressure level for the gas analyzer system to analyze an air sample collected from the diverted air during movement of the diverted air though a chamber in the air interface. A first airtight seal is present between the tube and the input port and a second airtight seal is present between a probe of the gas analyzer system and a sampling port of the air interface. The air sample is obtained from the diverted air as the diverted air moves through the chamber using the probe inserted through the sampling port in the air interface. The air sample is analyzed by the gas analyzer system to determine a set of components in the air sample.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Figure 1:
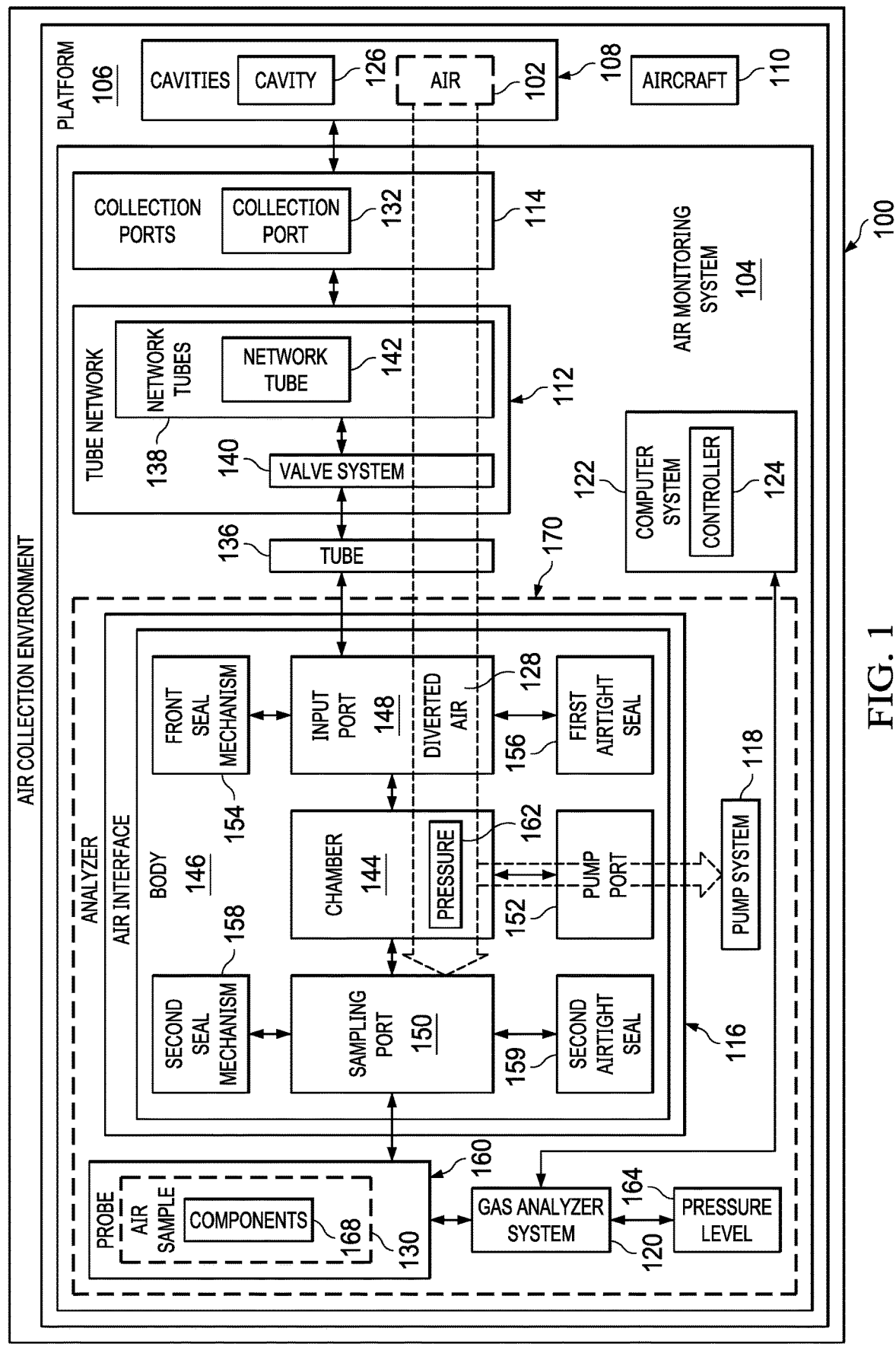
FIG. 1 is an illustration of a block diagram of an air collection environment in accordance with an illustrative embodiment.

The illustrative embodiments recognize and take into account one or more different considerations. For example, the illustrative embodiments recognize and take into account that gas chromatography mass spectrometers (GC-MS) can be used to analyze air samples. The illustrative embodiments recognize and take into account that a portable gas chromatography mass spectrometer unit can be moved from location to location in an aircraft to collect air samples in performing an airflow analysis for the aircraft.

The illustrative embodiments recognize and take into account that currently, portable gas chromatography mass spectrometer may need to be within three feet of the location from which an air sample is to be collected. The illustrative embodiments recognize and take into account that currently, the portable gas chromatography mass spectrometer may be unable to be positioned in or close enough to a cavity to collect an air sample for airflow analysis with this type of distance limitation. The illustrative embodiments recognize and take into account that access issues can be present for collecting the air samples from cavities in different locations. For example, the illustrative embodiments recognize and take into account that the cavities, such as the areas between insulation blankets and an aircraft skin for a fuselage, can be inaccessible or very difficult to access. Further, the illustrative embodiments recognize and take into account that the gas chromatography mass spectrometer may be unable to collect and analyze air that is pressurized at a pressure level greater than ambient atmospheric pressure.

Thus, the illustrative embodiments recognize and take into account that collecting the air samples for analysis may be more difficult than desired with currently used gas chromatography mass spectrometers.

Thus, the illustrative embodiments provide a method, apparatus, and system for collecting air samples without the need for the collection and testing apparatus to be in close proximity to the air sample, and in embodiments, provides the ability to collect and analyze air that is not pressurized. In addition, the illustrative embodiments reduce the need for lengthy tubing for collecting samples. Further, the illustrative embodiments provide for use of the air monitoring system in real-time. In one illustrative example, an air monitoring system comprises an air interface. The air interface has a body, a first seal mechanism, and a second seal mechanism. In this example, the body has a chamber with a first input port, a sampling port, and a pump port.

In this illustrative example, the chamber in the body is in fluid communication with the input port, the sampling port, and the pump port. The first seal mechanism is connected to the input port. The first seal mechanism forms a first airtight seal at the input port when a tube is connected to the input port. The second seal mechanism is connected to the sampling port. The second seal mechanism forms a second airtight seal at the sampling port when a probe for a gas analyzer system is inserted into the sampling port.

Diverted air can move into the input port, through the chamber, and out of the pump port without increasing a pressure of the diverted air greater than a pressure level for the gas analyzer system to analyze an air sample from the diverted air when the diverted air is drawn through the chamber and out of the pump port. A probe can obtain the air sample from the diverted air moving through the chamber. This air sample can be analyzed to identify components in the air sample. This analysis can be used for various purposes such as design changes or real-time air quality monitoring.

With reference now to the figures and, in particular, with reference to FIG. 1, an illustration of a block diagram of an air collection environment is depicted in accordance with an illustrative embodiment. In this illustrative example, air collection environment 100 is an environment in which air 102 can be collected for analysis.

As depicted, air monitoring system 104 can collect air 102 from platform 106. In this illustrative example, platform 106 can take a number of different forms. For example, platform 106 can comprise one or more of a mobile platform, a stationary platform, a land-based structure, an aquatic-based structure, a space-based structure, an aircraft, a commercial aircraft, a rotorcraft, a tilt-rotor aircraft, a tilt wing aircraft, a vertical takeoff and landing aircraft, a surface ship, a cruise ship, a tank, a personnel carrier, a train, a spacecraft, a space station, a satellite, a submarine, an automobile, a power plant, a dam, a house, a manufacturing facility, and a building.

In this illustrative example, air monitoring system 104 can collect air 102 from a set of cavities 108 in platform 106. As used herein, a "set of," when used with reference to items, means one or more items. For example, a "set of cavities 108" is one or more of cavities 108. In this illustrative example, when platform 106 takes the form of aircraft 110, the set of cavities 108 can comprise at least one of an area between the outer skin of aircraft 110 and an insulation blanket layer, a passenger cabin, a galley, a cargo area, a cockpit, or some other suitable space within aircraft 110.

As used herein, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

As depicted, air monitoring system 104 can comprise a number of different components. For example, air monitoring system 104 can comprise tube network 112, a set of collection ports 114, air interface 116, pump system 118, gas analyzer system 120, computer system 122, and controller 124.

As depicted, the different components in air monitoring system 104 can move air 102 from cavity 126 in the set of cavities 108 as diverted air 128 to gas analyzer system 120 such that gas analyzer system 120 can collect air sample 130 from diverted air 128 for analysis. As a result, gas analyzer system 120 can remotely analyze air 102 in cavity 126. This type of configuration reduces issues with moving portable gas analyzers to locations for real-time monitoring of air quality in platform 106. This type of configuration can also reduce issues with access to various locations in the set of cavities 108 in platform 106.

In this illustrative example, air 102 is moved from cavity 126 as diverted air 128 to gas analyzer system 120 through the set of collection ports 114, tube network 112, and air interface 116. For example, collection port 132 in the set of collection ports 114 for cavity 126 is in communication with cavity 126. In this illustrative example, collection port 132 can be in communication with cavity 126 by being located within cavity 126, being located in the opening to cavity 126, or in some other suitable location that allows movement of air 102 from cavity 126 into collection port 132 as diverted air 128.

In this illustrative example, the set of collection ports 114 including collection port 132 is connected to tube network 112 such that the set of collection ports 114 is in fluid communication with tube network 112. Additionally, air interface 116 is connected to and in fluid communication with tube network 112. In this illustrative example, air interface 116 is connected to tube 136 which is connected to tube network 112. In some illustrative examples, tube 136 can be considered part of tube network 112.

In this illustrative example, tube network 112 comprises network tubes 138 and valve system 140. Network tubes 138 are connected to the set of collection ports 114 and to valve system 140. As depicted, tube 136 is also connected to valve system 140. Valve system 140 can operate to select collection port 132 in the set of collection ports 114 to be in communication with tube 136 such that air 102 is moved from cavity 126 in which collection port 132 is located as diverted air 128 through network tube 142 in network tubes 138 and into tube 136 connected to valve system 140 in tube network 112. Diverted air 128 can then move through air interface 116.

In this illustrative example, network tubes 138 and other tubes used in air monitoring system 104 can be selected from at least one of rigid tubes, flexible tubes, or other suitable types of tubes. These tubes can be comprised of materials that reduce the introduction of contaminants or the absorption of components in diverted air 128 moving through the tubes.

In illustrative example, the use of the term "in communication" or "in fluid communication" between different components means that at least one of air, other gases, or fluids can be moved between the different components.

As depicted, gas analyzer system 120 can be connected to air interface 116. Gas analyzer system 120 can collect air sample 130 from diverted air 128 flowing through tube 136 and air interface 116.

In this illustrative example, air interface 116 comprises chamber 144 in body 146. Chamber 144 is in fluid communication with input port 148, sampling port 150, and pump port 152.

As depicted, air interface 116 also includes first seal mechanism 154 connected to input port 148. First seal mechanism 154 can form first airtight seal 156 at input port 148 when tube 136 is connected to input port 148. Second seal mechanism 158 for air interface 116 is connected to sampling port 150. Second seal mechanism 158 can form second airtight seal 159 at sampling port 150 when probe 160 for gas analyzer system 120 is connected to sampling port 150. The connection of probe 160 can be performed by inserting probe 160 through sampling port 150 into chamber 144 in body 146 of air interface 116.

In the illustrative example, these seal mechanisms can be comprised of a number of different types of materials. For example, the seal mechanisms can be manufactured using at least one of a synthetic rubber, a thermoset polymer, a thermoplastic polymer, butadiene rubber (BR), butyl rubber (IIR), a chlorosulfonated polyethylene (CSM), an ethylene propylene diene monomer (EPDM), an ethylene propylene rubber (EPR), fluoroelastomer (FKM), a nitrile rubber, a silicon rubber, a polyurethane, an ether-ester elastomer, a co-polyester, other suitable materials, or combinations thereof.

The selection of the material can be such that contaminants are not introduced into diverted air 128 flowing into and through air interface 116.

Additionally, the selection of the material can also be such that the seals do not absorb or retain components 168 that may be present in diverted air 128 when air sample 130 is collected.

In this illustrative example, air interface 116 comprises a set of materials that avoids introducing a contaminant into air sample 130 or absorbing components from air sample 130. For example, air interface 116 can comprise a set of materials selected from a group consisting of a metal, a plastic, a ceramic, and combinations thereof. The metal can be selected from one or more of aluminum, titanium, nickel, stainless steel, and alloys thereof.

During the movement of diverted air 128 into input port 148, through chamber 144, and out of pump port 152, diverted air 128 can be moved by pump system 118 without increasing pressure 162 of diverted air 128 greater than pressure level 164 for gas analyzer system 120 to obtain and analyze air sample 130 from diverted air 128 when diverted air 128 is drawn through chamber 144 and out of pump port 152 by pump system 118. In this example, probe 160 obtains air sample 130 from diverted air 128 moving through chamber 144. Pressure 162 of diverted air 128 can be an ambient atmospheric pressure. In this illustrative example, pressure 162 of diverted air 128 is the pressure present when air sample 130 is collected by gas analyzer system 120.

In this illustrative example, operation of pump system 118 and gas analyzer system 120 can be controlled by controller 124 in computer system 122. Further, controller 124 can also control the operation of valve system 140 in tube network 112.

Controller 124 can be implemented in software, hardware, firmware, or a combination thereof. When software is used, the operations performed by controller 124 can be implemented in program code configured to run on hardware, such as a processor unit. When firmware is used, the operations performed by controller 124 can be implemented in program code and data and stored in persistent memory to run on a processor unit. When hardware is employed, the hardware can include circuits that operate to perform the operations in controller 124.

In the illustrative examples, the hardware can take a form selected from at least one of a circuit system, an integrated circuit, an application specific integrated circuit (ASIC), a programmable logic device, or some other suitable type of hardware configured to perform a number of operations. With a programmable logic device, the device can be configured to perform the number of operations. The device can be reconfigured at a later time or can be permanently configured to perform the number of operations. Programmable logic devices include, for example, a programmable logic array, a programmable array logic, a field programmable logic array, a field programmable gate array, and other suitable hardware devices. Additionally, the processes can be implemented in organic components integrated with inorganic components and can be comprised entirely of organic components excluding a human being. For example, the processes can be implemented as circuits in organic semiconductors.

Computer system 122 is a physical hardware system and includes one or more data processing systems. When more than one data processing system is present in computer system 122, those data processing systems are in communication with each other using a communications medium. The communications medium can be a network. The data processing systems can be selected from at least one of a computer, a server computer, a tablet computer, or some other suitable data processing system.

In the illustrative example, controller 124 can control pump system 118 to move air 102 from collection port 132 for cavity 126 as diverted air 128 to tube 136 connected to collection port 132, move diverted air 128 into input port 148 of air interface 116 connected to tube 136, through chamber 144 of air interface 116, and out of pump port 152 of air interface 116 without increasing pressure 162 of diverted air 128 greater than pressure level 164 for gas analyzer system 120 to analyze air sample 130 collected from diverted air 128. Collection port 132 can be at a location in cavity 126 in platform 106. An airtight seal, such as first airtight seal 156, is present between tube 136 and input port 148.

Additionally, controller 124 can also control gas analyzer system 120 connected to sampling port 150 in air interface 116 by probe 160 to obtain air sample 130 from diverted air 128 moving through air interface 116 and analyze air sample 130 to determine a set of components 168 in air sample 130 drawn from diverted air 128 by probe 160. In this illustrative example, gas analyzer system 120 can comprise one or more gas analyzers selected from at least one of a gas chromatography mass spectrometer, a proton transfer reaction mass spectrometer, a biosensor, an optical biosensor, an electrochemical biosensor, or a combination thereof.

Further, controller 124 can control valve system 140 to select collection port 132 to move air 102 as diverted air 128. This movement of diverted air 128 occurs through valve system 140 connecting network tube 142 in network tubes 138 to tube 136 enabling communication from collection port 132 to air interface 116. In other words, valve system 140 can change configurations to select different network tubes in network tubes 138 to enable diverted air 128 to be drawn from air 102 in a selected cavity in the set of cavities 108.

In one illustrative example, one or more technical solutions are present that overcome a problem with collecting air samples from different locations in platform 106, such as aircraft 110. As a result, one or more illustrative examples can provide a solution in which air monitoring system 104 operates to enable a gas analyzer system to divert air 102 from one or more cavities 108 in aircraft 110 in a manner that enables gas analyzer system 120 to obtain air sample 130 from diverted air 128 for analysis. In the illustrative example, air interface 116 is constructed such that diverted air 128 can flow through air interface 116 with pressure 162 at pressure level 164 that allows gas analyzer system 120 to obtain air sample 130 for analysis.

The construction of air interface 116 can be based on one or more dimensions of air interface 116. For example, the dimensions can be selected such that pressure level 164 for pressure 162 of diverted air 128 is not greater than what gas analyzer system 120 can use to collect and analyze air sample 130.

Gas analyzer system 120 can be sensitive to pressure 162 operating to obtain and analyze air sample 130. If pressure 162 of diverted air 128 is greater than pressure level 164 that can be used by gas analyzer system 120, gas analyzer system 120 may be unable to obtain air sample 130 in a manner needed to properly analyze air sample 130 to obtain a desired level of accuracy in the analysis.

Further, air monitoring system 104 in the illustrative example can overcome an issue with real-time monitoring of air quality in aircraft 110 using a portable gas analyzer such as a portable gas chromatography mass spectrometry (GC-MS) unit. The use of air interface 116 with tube network 112 connected to collection ports 114 in different locations in aircraft 110 allows for continuously monitoring air 102 for air quality and variations in real-time without the distance and access limitations of a portable gas chromatography mass spectrometry unit.

The illustration of air collection environment 100 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, components such as air interface 116, gas analyzer system 120, and pump system 118 can be grouped to form analyzer 170. In some illustrative examples, multiple analyzers can be present for platform 106. In yet other illustrative examples, computer system 122 can be considered part of analyzer 170 and can be in communication with multiple analyzers to control their operation. As another example, a single air interface is shown in the depicted example in air collection environment 100. In other illustrative examples, one or more air interfaces can be present in addition to or in place of air interface 116. These air interfaces can connect to one or more gas analyzers within gas analyzer system 120 to tube network 112. In yet other illustrative examples, one or more tube networks may be present in addition to tube network 112 within platform 106. For example, when platform 106 is aircraft 110, one tube network may be in communication with cavities 108 located between an insulation layer and the skin of aircraft 110. Another tube network may be in communication with cavity 126 in the form of a passenger cabin in aircraft 110. In another example, tube network 112 can be in communication with another cavity in cavities 108 such as a cargo hold or flight deck of aircraft 110.

Figure 2:
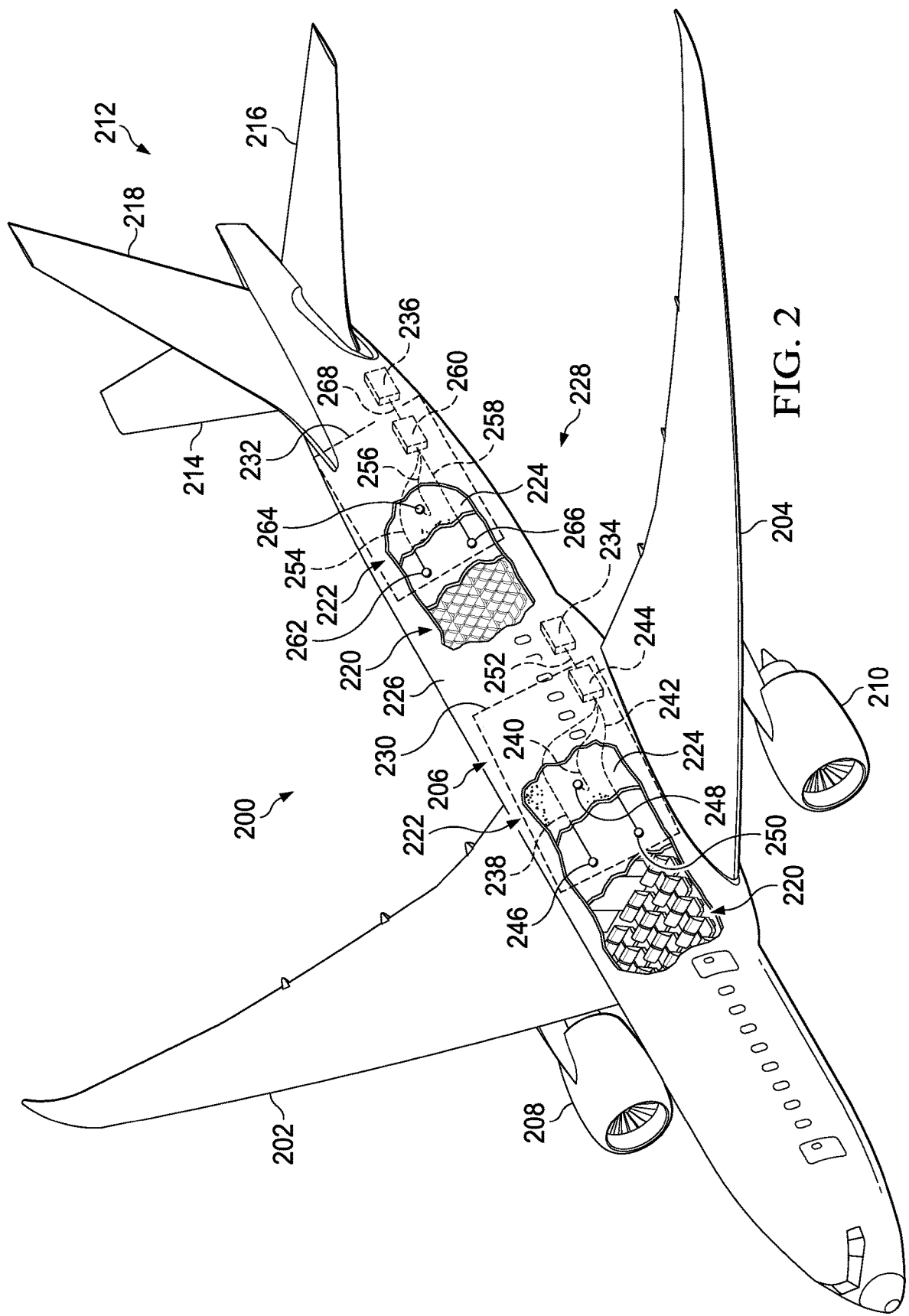
FIG. 2 is an illustration of an aircraft with an air monitoring system in accordance with an illustrative embodiment.

With reference next to FIG. 2, an illustration of an aircraft with an air monitoring system is depicted in accordance with an illustrative embodiment. In this illustrative example, commercial passenger aircraft 200 is an example of one implementation for aircraft 110 shown in block form in FIG. 1. In this illustrative example, commercial passenger aircraft 200 takes the form of a commercial passenger aircraft with fixed wings.

As depicted, commercial passenger aircraft 200 has wing 202 and wing 204 attached to body 206. Commercial passenger aircraft 200 includes engine 208 attached to wing 202 and engine 210 attached to wing 204.

Body 206 has tail section 212. Horizontal stabilizer 214, horizontal stabilizer 216, and vertical stabilizer 218 are attached to tail section 212 of body 206.

In this illustrative example, cavities in the interior of commercial passenger aircraft 200 can be seen within body 206 in this exposed view. As depicted in this exposed view, the cavities seen within commercial passenger aircraft 200 include portions of passenger cabin 220 and spaces between insulation layer 224 and skin 226 of body 206. In this illustrative example, insulation layer 224 comprises insulation blankets.

Spaces 222 and passenger cabin 220 are examples of cavities 108 shown in block form in FIG. 1. Other cavities that can be present in commercial passenger aircraft 200 but not shown in this exposed view include a flight deck, a cargo area, a galley, a laboratory, or other suitable spaces.

In this illustrative example, air monitoring system 228 is located in commercial passenger aircraft 200 to detect at least one of air quality or airflow within commercial passenger aircraft 200. This detection can be performed in real-time or at a later time using information logs resulting from sampling air within commercial passenger aircraft 200.

In this illustrative example, air monitoring system 228 comprises a number of different components. As depicted, air monitoring system 228 comprises tube network 230, tube network 232, analyzer 234, and analyzer 236.

As depicted in this example, tube network 230 comprise tubes such as network tube 238, network tube 240, and network tube 242 connected to valve system 244. As depicted, network tube 238 is connected to collection port 246, which can divert air from passenger cabin 220 in spaces 222; network tube 240 is connected to collection port 248, which can divert air from passenger cabin 220 in spaces 222; and network tube 242 is connected to collection port 250, which can divert air from passenger cabin 220 in spaces 222. In this example, valve system 244 is connected to an air interface in analyzer 236 by tube 252.

In this illustrative example, tube network 232 comprise tubes such as network tube 254, network tube 256, and network tube 258 connected to valve system 260. As depicted, network tube 254 is connected to collection port 262, which can divert air from passenger cabin 220 in spaces 222; network tube 256 is connected to collection port 264, which can divert air from passenger cabin 220 in spaces 222; and network tube 258 is connected to collection port 266, which can divert air from passenger cabin 220 in spaces 222. In this example, valve system 260 is connected to an air interface in analyzer 236 by tube 268.

The illustration of commercial passenger aircraft 200 is not meant to limit the manner in which an illustrative example can be implemented in an aircraft. For example, other commercial passenger aircraft may include an upper passenger cabin and a lower passenger cabin separated by a deck. Although not shown, commercial passenger aircraft 200 also includes cavities in the form of cargo areas in which air quality monitoring can be performed. In other illustrative examples, air monitoring system 228 can be used in other types of aircraft other than commercial passenger aircraft 200. Other types of aircraft in which an illustrative example can be implemented include, for example, a rotorcraft, a tiltrotor aircraft, a tilt wing aircraft, a vertical takeoff and landing aircraft, a military jet, a cargo aircraft, a cargo jet, or other suitable type of aircraft.

Figure 3:
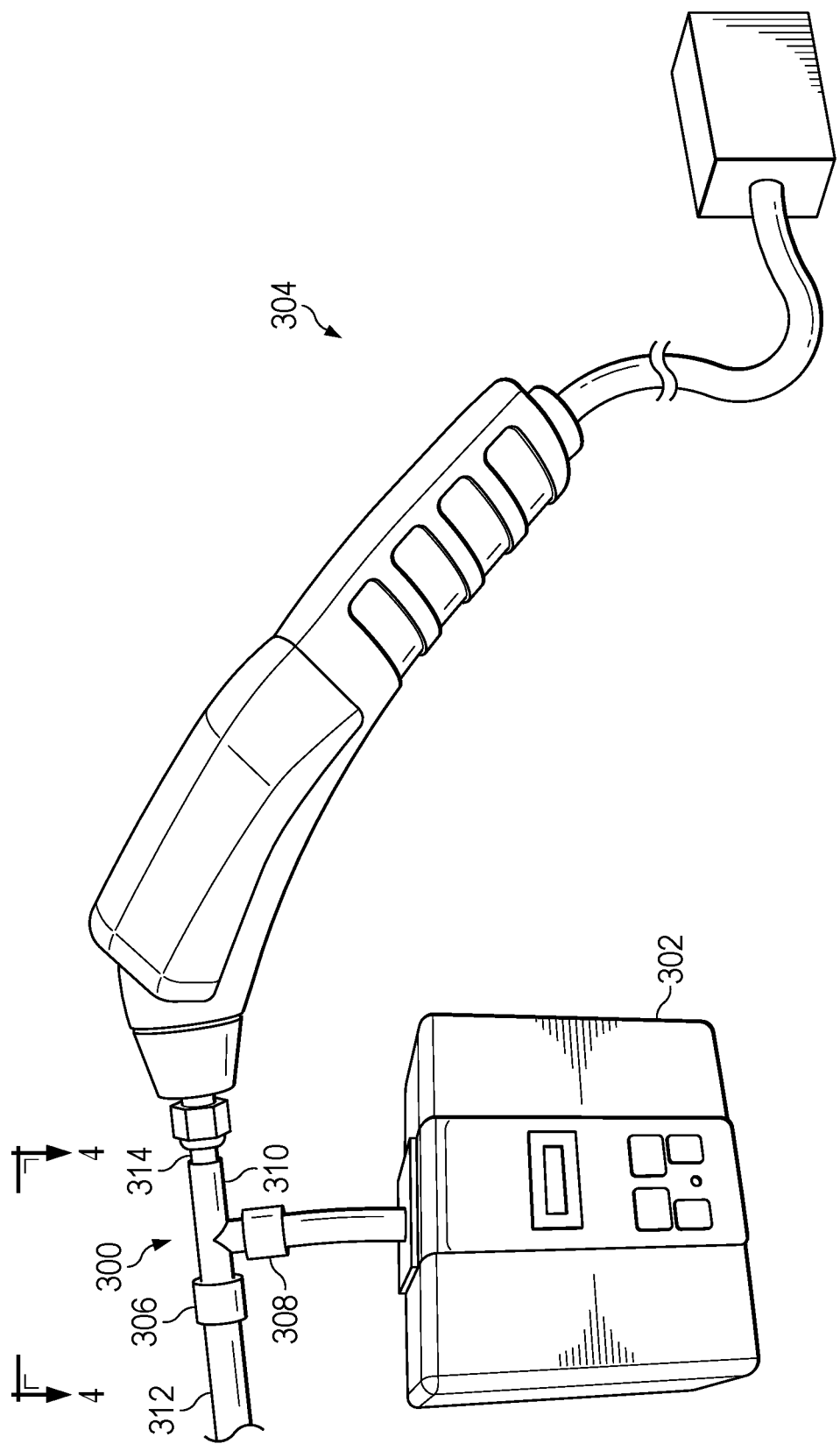
FIG. 3 is an illustration of components in an analyzer in accordance with an illustrative embodiment.

Turning now to FIG. 3, an illustration of components in an analyzer is depicted in accordance with an illustrative embodiment. The components illustrated in FIG. 3 are examples of components that can be found in analyzer 170 in FIG. 1, analyzer 234 in FIG. 2, and analyzer 236 in FIG. 2. As depicted, these components include air interface 300, pump 302, and gas analyzer 304.

As depicted, air interface 300 has input port 306, pump port 308, and sampling port 310.

In this illustrative example, tube 312 is connected to input port 306 in air interface 300. Tube 312 is also connected to a valve system such as valve system 140 in FIG. 1, valve system 244 in FIG. 2, and valve system 260 in FIG. 2.

As depicted, tube 312 connects pump 302 to input port 306 in air interface 300. In this illustrative example, probe 314 for gas analyzer 304 is connected to sampling port 310 in air interface 300.

In this illustrative example, pump 302 can operate to pump diverted air through tube 312 into input port 306 and out through pump port 308. With the movement of the diverted air, gas analyzer 304 can obtain an air sample using probe 314 inserted into sampling port 310. In this illustrative example, pump 302 operates such that the pressure of the diverted air is at a level that enables gas analyzer 304 to obtain an air sample for analysis.

Figure 4:
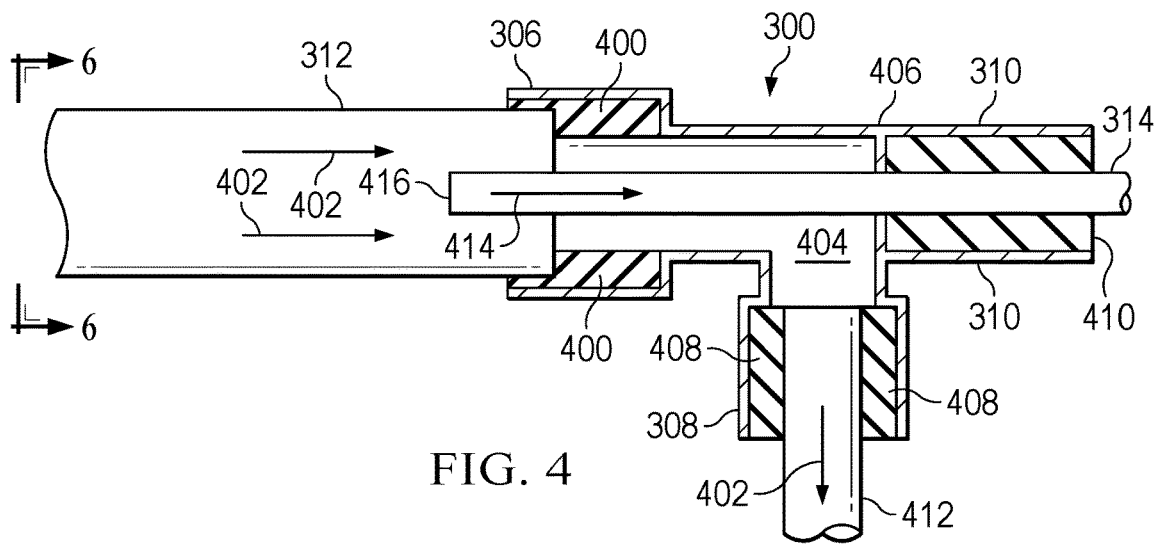
FIG. 4 is an illustration of a cross-sectional view of an air interface in accordance with an illustrative embodiment.

With reference next to FIG. 4, an illustration of a cross-sectional view of an air interface is depicted in accordance with an illustrative embodiment. In the illustrative examples, the same reference numeral may be used in more than one figure. This reuse of a reference numeral in different figures represents the same element in the different figures. In this figure, a cross-sectional view of air interface 300 is shown taken along lines 4-4 in FIG. 3.

In this cross-sectional view, body 406 of air interface 300 has a T-shape. In this view, tube 312 is shown as being connected to input port 306. In this illustrative example, the connection is made by inserting tube 312 into input port 306.

Further, an airtight seal is formed between tube 312 and input port 306. This seal can be formed using seal 400. Seal 400 is a mechanical seal that aids in joining tube 312 to input port 306 in a manner that prevents leakage of diverted air 402 flowing through tube 312 into chamber 404 inside body 406 of air interface 300 through input port 306. As depicted, seal 400 is an O-ring seal. In this illustrative example, an airtight seal can also be formed between tube 412 and pump port 308 using seal 408, which can also be an O-ring seal.

As depicted, probe 314 is inserted through sampling port 310. An airtight seal can also be formed between probe 314 and sampling port 310 using seal 410. As depicted, seal 410 can also take the form of an O-ring seal. In the illustrative example, the airtight seals at the different ports can reduce or prevent contaminants from being introduced into diverted air 402 as diverted air 402 flows from tube 312 into input port 306 through chamber 404 and body 406 and out through tube 412 connected to pump port 308.

In this illustrative example, probe 314 is inserted into sampling port 310 that probe 314 extends through chamber 404 and input port 306. In this illustrative example, end 416 of probe 314 extends through input port 306 into tube 312. This position of probe 314, with end 416 being located within tube 312, can reduce concerns that contaminants may be introduced into diverted air 402 or components may be removed from diverted air 402 by various materials that may be used to construct body 406, seal 400, seal 408, and seal 410. With this position, air sample 414 is collected by probe 314 from diverted air 402 prior to diverted air 402 moving through body 406 of air interface 300.

Figure 5:
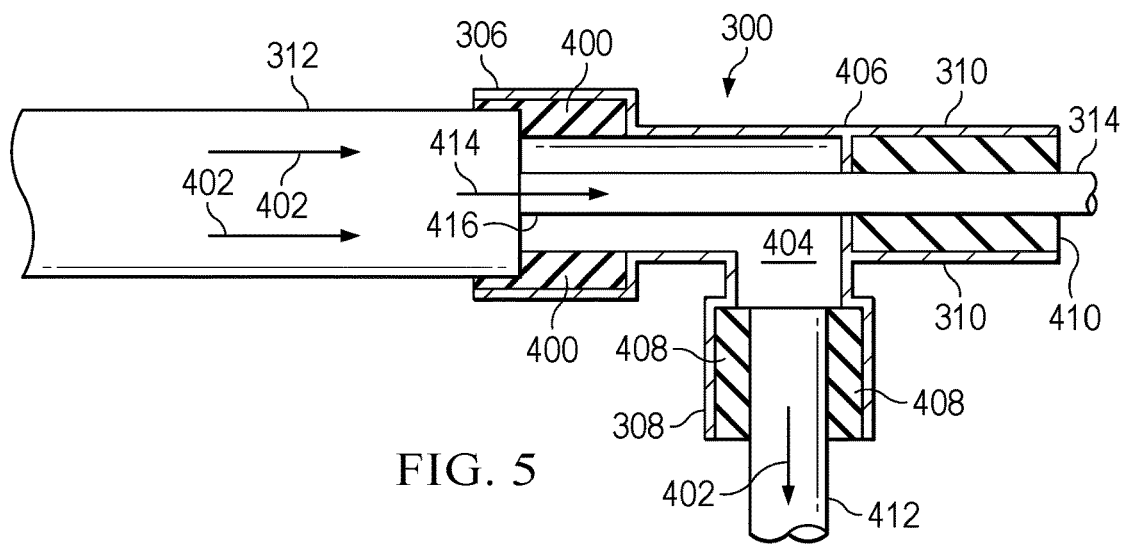
FIG. 5 is an illustration of a cross-sectional view of an air interface in accordance with an illustrative embodiment.

With reference to FIG. 5, an illustration of a cross-sectional view of an air interface is depicted in accordance with an illustrative embodiment. In this figure, a cross-sectional view of air interface 300 is shown taken along lines 4-4 in FIG. 3.

As depicted in this view, probe 314 does not extend into tube 312. As depicted, end 416 of probe 314 remains within body 406 of air interface 300. As illustrated in this example, probe 314 extends through sampling port 310, chamber 404, and into input port 306.

Figure 6:
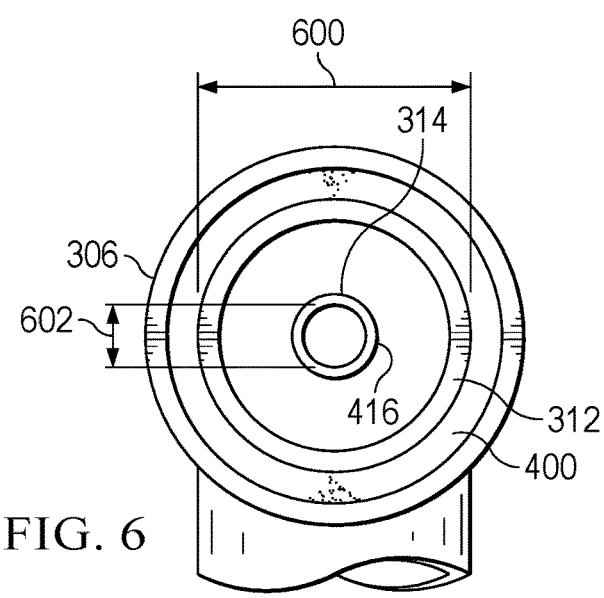
FIG. 6 is an illustration of a cross-sectional view in accordance with an illustrative embodiment.

With now reference to FIG. 6, an illustration of a cross-sectional view is depicted in accordance with an illustrative embodiment. A cross-sectional view of air interface 300 is shown taken along lines 6-6 in FIG. 4. This view shows a visualization of diameters for tube 312, seal 400, input port 306, and probe 314. In this illustrative example, tube 312 has first diameter 600 and probe 314 has second diameter 602.

As depicted, first diameter 600 for tube 312 is larger than second diameter 602 of probe 314. In this example, first diameter 600 and second diameter 602 have a ratio of approximately 3.5:1. This ratio is one example of a dimension that may be used for air interface 300.

In this illustrative example, the ratios can be selected to obtain a desired flow rate of diverted air 402 without increasing the pressure of diverted air 402 to a level greater than can be present for the gas analyzer to operate to obtain air sample 414 for analysis. This ratio can also be selected based on the operation of the pump drawing diverted air 402. For example, the rate at which air flows when the pump pulls air can be taken into consideration with selecting the ratios to obtain the desired pressure for diverted air 402.

The illustration of air interface 300 in FIGS. 3-6 is an example of one manner in which air interface 116 shown in block form in FIG. 1 can be implemented. In other illustrative examples, the air interface can have a different shape other than a T-shape. For example, the air interface can have a Y-shape or other suitable shape. Further, in other illustrative examples, end 416 of probe 314 may extend into tube 312 while remaining in input port 306 when tube 312 is connected to input port 306 by being inserted into input port 306.

Figure 7:
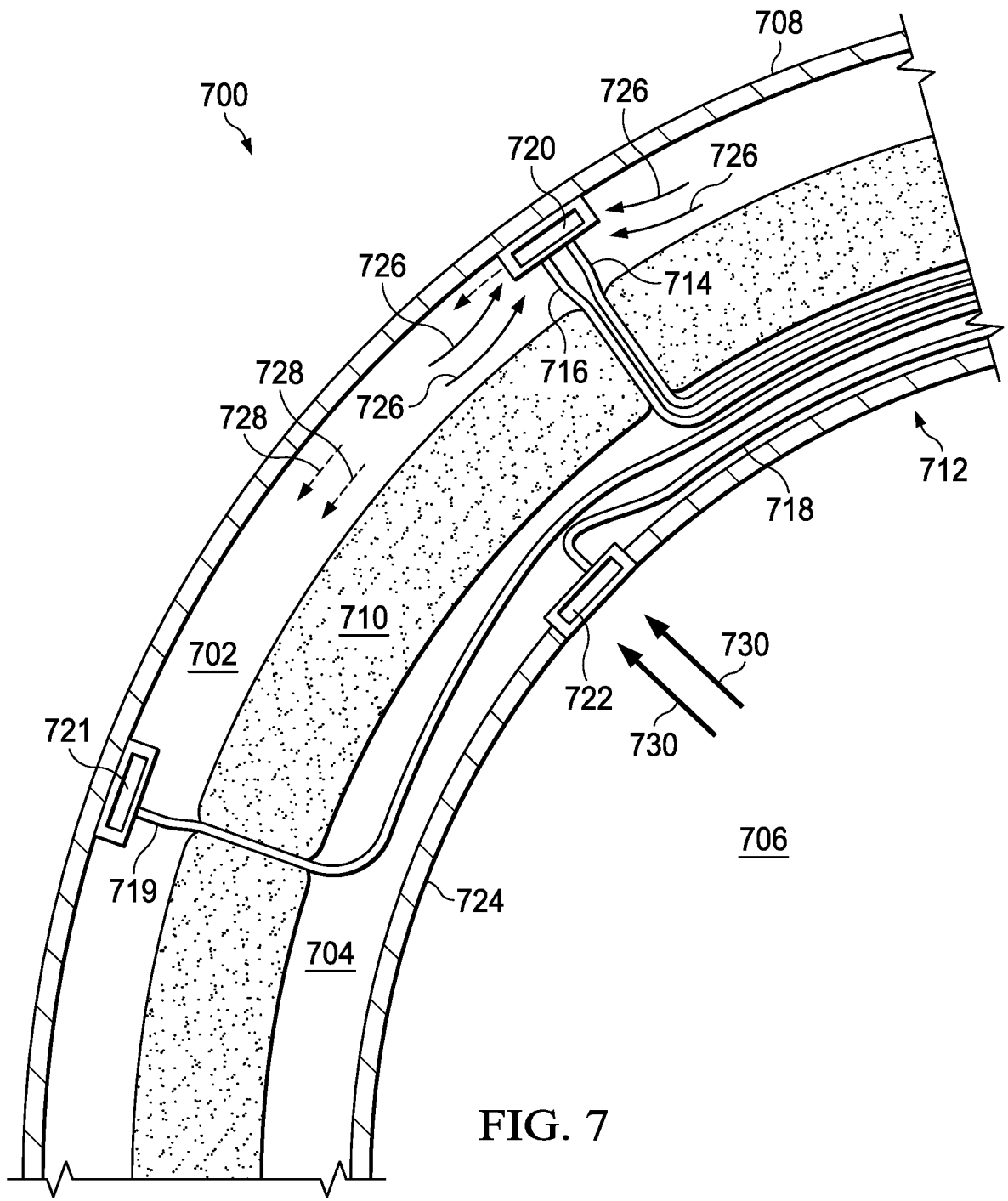
FIG. 7 is an illustration of a cross-section of a portion of a body of an aircraft in accordance with an illustrative embodiment.

Turning next to FIG. 7, an illustration of a cross-section of a portion of a body of an aircraft is depicted in accordance with an illustrative embodiment. In this depicted example, body 700 is an example of a structure or fuselage for an aircraft such as aircraft 110 shown in block form in FIG. 1 or for commercial passenger aircraft 200 in FIG. 2.

In this illustrative example, cavities are present within body 700. As depicted, cavity 702, cavity 704, and cavity 706 can be seen in this cross-sectional view of a portion of body 700.

Cavity 702 is the space between skin 708 and insulation layer 710 of body 700. Insulation layer 710 can be comprised of insulation blankets. Cavity 702 is a cavity in which moisture can at least one of collect, condense, or freeze during operation of an aircraft.

In this example, cavity 706 is an interior cavity within body 700. For example, cavity 706 can be a passenger cabin or a flight deck of the aircraft.

As depicted, cavity 704 is a location where tube network 712 can run within body 700. In this illustrative example, tube network 712 comprises tube 714, tube 716, tube 718, and tube 719. These tubes can be indirectly connected to a gas analyzer through a valve system or can be directly connected to the gas analyzer depending on the particular implementation.

In this illustrative example, collection port 720 is located in cavity 704. Collection port 720 is located on skin 708 in this illustrative example. In other depicted examples, collection port 720 can be located on insulation layer 710 or located in some other location in cavity 702 between skin 708 and insulation layer 710. As depicted, collection port 720 is connected to tube 714 and tube 716.

Collection port 720 is a device that provides an opening to collect air 726 located within cavity 702 such that air 726 can be moved through at least one of tube 714 or tube 716 as diverted air. In one illustrative example, gas 728 can be introduced into cavity 702 though tube 716 and air 726 can be collected through tube 714. Depending on the implementation, both tubes can introduce gas 728 into cavity 702 or collect air 726 from cavity 702. In this illustrative example, the gas can take a number of different forms. For example, the gas can be selected as one that can be detected by a gas analyzer. For example, the gas can be xenon or some other noble or inert gas. The particular gas can be selected as one that can be odorless, colorless, and have a desired level of chemical reactivity. Other examples of gases that may be selected include helium, neon, and argon.

In this example, gas 728 introduced at the location of collection port 720 can travel within cavity 702. Gas 728 can be detected in air 726 in another location in cavity 702 at collection port 721. In this example, collection port 721 is located on skin 708 within cavity 702.

Air 726 can be moved through tube 719 as diverted air. Additionally, this diverted air can also include gas 728. The time for gas 728 to travel from a first location at collection port 720 to a second location at collection port 721 can be determined to calculate air from within cavity 702 between those two locations. In the calculation, the time between the introduction of gas 728 and the detection of gas 728 can be adjusted to take into account travel time to reach a gas analyzer from tube 719 and other parts of tube network 712.

In this example, collection port 722 is located in ceiling structure 724. As depicted, ceiling structure 724 is a structural component that separates crown area of aircraft from the passenger cabin, flight deck, or other interior areas. Collection port 722 is connected to tube 718 in tube network 712. In this example, collection port 722 can provide an opening to collect air 730 from cavity 706. Air 730 collected from cavity 706 can be moved through tube 718 as diverted air for analysis by the gas analyzer.

This analysis can be used to determine air quality within cavity 706. This type of analysis can be performed in real-time during operation of the aircraft. With multiple collection ports in communication with cavity 706, the air quality in different parts of cavity 706 can be determined. An indication of an undesired air quality such as an odor can be used to locate the source of an odor to reduce or cease generation of the odor.

Figure 8:
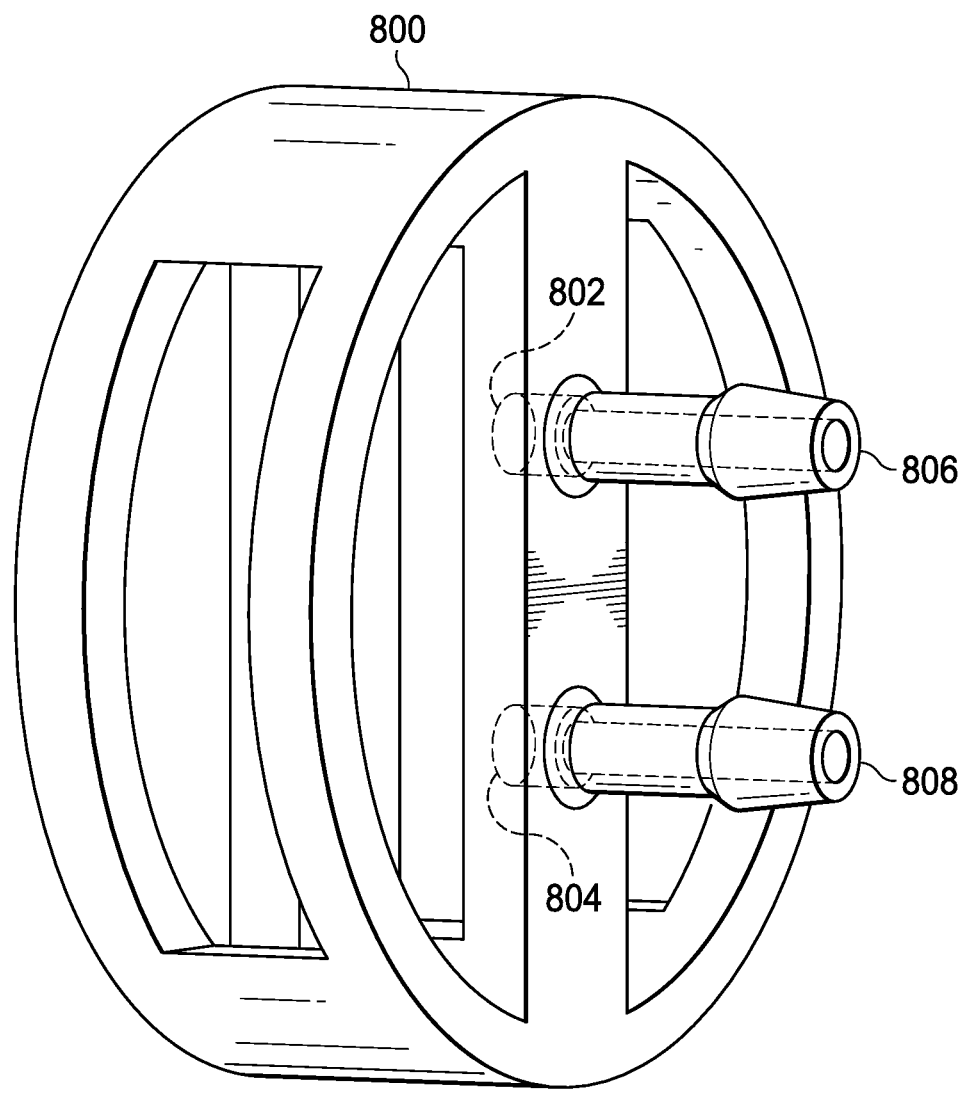
FIG. 8 is an illustration of a collection port in accordance with an illustrative embodiment.

With reference now to FIG. 8, an illustration of a collection port is depicted in accordance with an illustrative embodiment. Collection port 800 is an example of one implementation for collection port 132 and other collection ports in collection ports 114 in FIG. 1. Collection port 800 can also be an example implementation for one or more of collection port 246, collection port 248, collection port 250, collection port 262, collection port 264, and collection port 266 in FIG. 2. Collection port 800 can also be used to implement collection port 720, collection port 721, and collection port 722 in FIG. 7.

Collection port 800 can be comprised of a number of different types of materials. For example, one or more materials can be selected based on factors such as weight and different temperatures to which collection port 800 may be exposed. Additionally, the material can be selected as material that reduces at least one of the introduction of contaminants or the absorption of components from air drawn through collection port 800.

In this illustrative example, collection port 800 has opening 802 and opening 804 through which air can be drawn from a cavity. Opening 802 leads to connector 806 and opening 804 leads to connector 808.

These two connectors can be connected to tubes to draw air into the tubes for movement as diverted air. In one illustrative example, opening 802 and connector 806 can be connected to a tube that introduces a gas into the cavity while opening 804 and connector 808 can be connected to a tube that draws air from the cavity. In this illustrative example, when used to implement collection port 721 and collection port 722 in FIG. 7, collection port 800 has a single opening and connector.

The illustrations of collection ports and the tube network in FIG. 7 and FIG. 8 are presented for purposes of showing one illustrative example of how different components can be implemented. These illustrations are not meant to limit the manner in which other illustrative examples can be implemented. For example, other numbers of tubes and collection ports can be used in the portion of the aircraft displayed. As another example, the collection ports can have a different shape other than the cylindrical shape shown in FIG. 7 and FIG. 8. For example, a collection port can have a shape of a hemisphere, a cube, a cuboid, a triangular prism, a square pyramid, or some other suitable shape that includes openings to draw air from a cavity.

Figure 9:
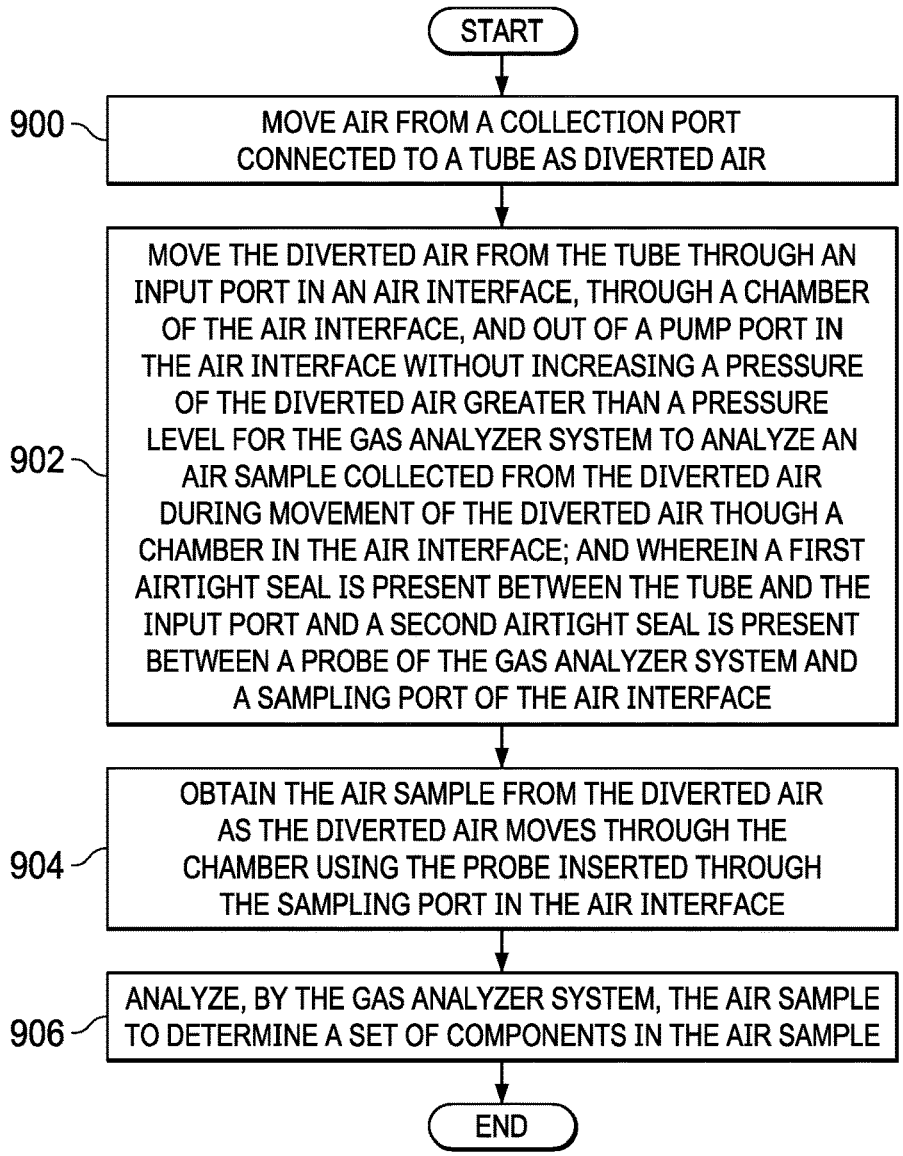
FIG. 9 is an illustration of a flowchart of a process for monitoring air in accordance with an illustrative embodiment.

Turning next to FIG. 9, an illustration of a flowchart of a process for monitoring air is depicted in accordance with an illustrative embodiment. The process in FIG. 9 can be implemented in hardware, software, or both. When implemented in software, the process can take the form of program code that is run by one or more processor units located in one or more hardware devices in one or more computer systems. For example, the process can be implemented in controller 124 in computer system 122 in FIG. 1. These different operations can be implemented in controller 124 to control the operation of different components in air monitoring system 104 in FIG. 1 to monitor air in a platform.

The process begins by moving air from a collection port connected to a tube as diverted air (operation 900). The process moves the diverted air from the tube through an input port in an air interface, through a chamber in the air interface, and out of a pump port in the air interface without increasing a pressure of the diverted air greater than a pressure level for a gas analyzer system to analyze an air sample collected from the diverted air during movement of the diverted air though a chamber in the air interface; and wherein a first airtight seal is present between the tube and the input port and a second airtight seal is present between a probe of the gas analyzer system and a sampling port of the air interface (operation 902).

The process obtains the air sample from the diverted air as the diverted air moves through the chamber using the probe inserted through the sampling port in the air interface (operation 904). The process analyzes, by the gas analyzer system, the air sample to determine a set of components in the air sample (operation 906). The process terminates thereafter.

Figure 10:
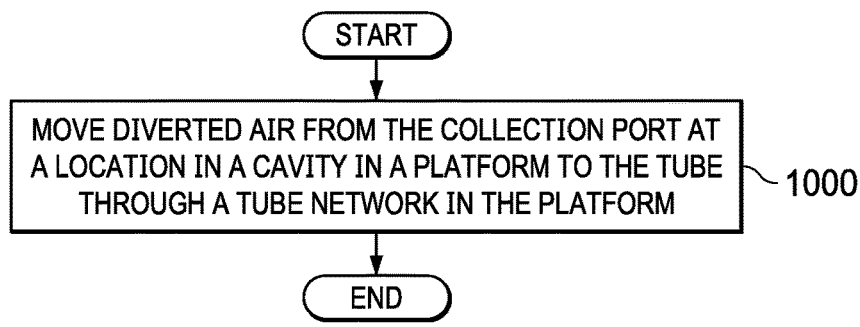
FIG. 10 is an illustration of a flowchart of a process for moving air in accordance with an illustrative embodiment.

Turning to FIG. 10, an illustration of a flowchart of a process for moving air is depicted in accordance with an illustrative embodiment. The operation in this flowchart is an example of an operation that can be performed with other operations in the flowchart in FIG. 9. In this example, a collection port is at a location in a cavity in a platform and a tube is connected to the collection port by a tube network in a platform.

The process moves diverted air from the collection port at a location in a cavity in a platform to the tube through a tube network in the platform (operation 1000). The process terminates thereafter.

This operation can be performed after the air is moved from the collection port as diverted air. The process can move the air to the tube through the tube network as described in operation 1000. This operation is optional and is not necessary when the tube is connected directly to the collection port.

Figure 11:
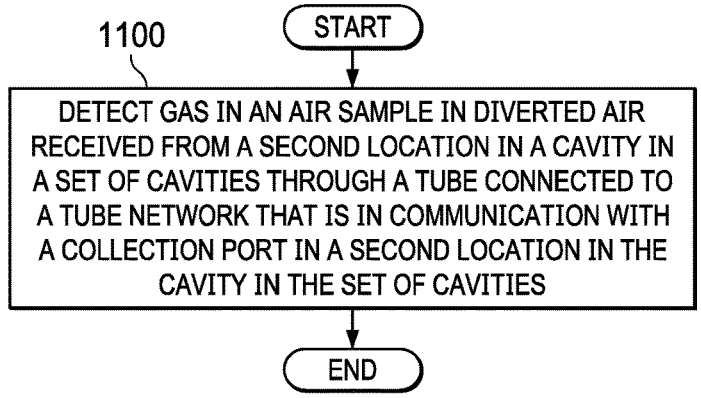
FIG. 11 is an illustration of a flowchart of a process for detecting a gas in an air sample in accordance with an illustrative embodiment.

With reference now to FIG. 11, an illustration of a flowchart of a process for detecting a gas in an air sample is depicted in accordance with an illustrative embodiment. The flowchart in FIG. 11 is an example of implementation for operation 906 in FIG. 9. In this example, a gas is injected into a set of cavities in a first location in a set of cavities and a collection port is located at a second location in the set of cavities in a platform.

The process begins by detecting a gas in an air sample in diverted air received from a second location in a cavity in a set of cavities through a tube connected to a tube network that is in communication with a collection port in the second location in the cavity in the set of cavities (operation 1100). The process terminates thereafter In this example, the gas is a component in the set of components.

Figure 12:
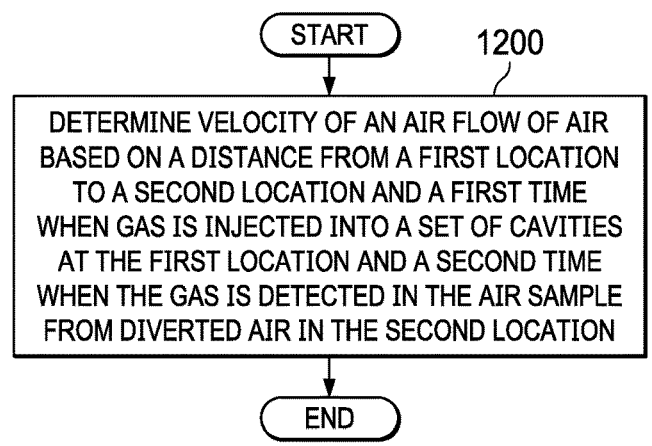
FIG. 12 is an illustration of a flowchart of a process for analyzing airflow in accordance with an illustrative embodiment.

In FIG. 12, an illustration of a flowchart of a process for analyzing airflow is depicted in accordance with an illustrative embodiment. The flowchart in FIG. 12 is an example of an operation that can be performed with the other operations in FIG. 9 and FIG. 11 using the gas detected as a component in the set of components in the air sample.

The process then begins by determining a velocity of an air flow of air based on a distance from a first location to a second location and a first time when the gas is injected into a set of cavities at the first location and a second time when the gas is detected in the air sample from the diverted air in the second location (operation 1200). The process terminates thereafter.

Figure 13:
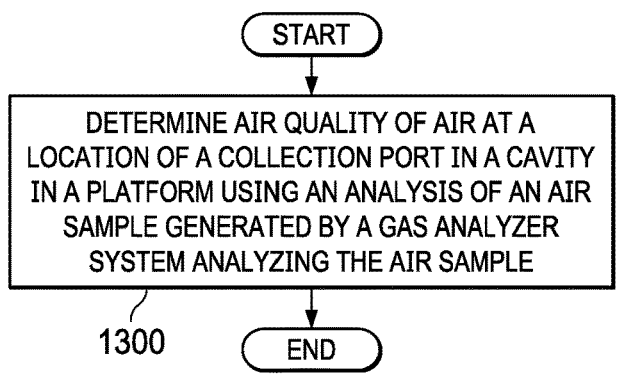
FIG. 13 is an illustration of a flowchart of a process for determining air quality in accordance with an illustrative embodiment.

Tuning to FIG. 13, an illustration of a flowchart of a process for determining air quality is depicted in accordance with an illustrative embodiment. The flowchart in FIG. 13 is an example of an operation that can be performed with the other operations in FIG. 9.

The process begins by determining air quality of air at a location of a collection port in a cavity in a platform using an analysis of an air sample generated by a gas analyzer system analyzing the air sample (operation 1300). The process terminates thereafter.

The operations in FIG. 13 can be performed in real-time by analyzing air samples as quickly as possible during operation of the platform. In other illustrative examples, the operations can be performed later based on analysis results of the air samples that have been logged or stored in a database.

The process illustrated in FIG. 13 can be used to determine the air quality at different locations in a platform. This analysis can be used to determine whether particular locations may need further analysis or whether changes may be needed to improve or change the air quality at particular locations. This information can also be used to generate air quality maps for a platform.

Figure 14:
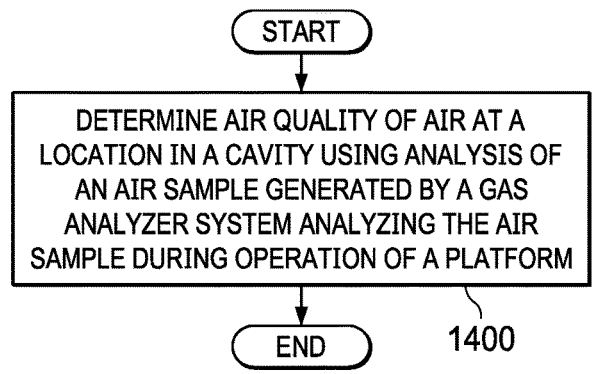
FIG. 14 is an illustration of a flowchart of a process for determining air quality in accordance with an illustrative embodiment.

With reference next to FIG. 14, an illustration of a flowchart of a process for determining air quality is depicted in accordance with an illustrative embodiment. The process illustrated in FIG. 14 is an example of one implementation for operation 1300 in FIG. 13.

The process determines air quality of air at a location in a cavity using an analysis of an air sample generated by a gas analyzer system analyzing the air sample during operation of a platform (operation 1400). The process terminates thereafter. In this manner, the air quality of the platform, such as an aircraft, can be monitored during flight of the aircraft.

The flowcharts and block diagrams in the different depicted embodiments illustrate the architecture, functionality, and operation of some possible implementations of apparatuses and methods in an illustrative embodiment. In this regard, each block in the flowcharts or block diagrams can represent at least one of a module, a segment, a function, or a portion of an operation or step. For example, one or more of the blocks can be implemented as program code, hardware, or a combination of the program code and hardware. When implemented in hardware, the hardware can, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams can be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 15:
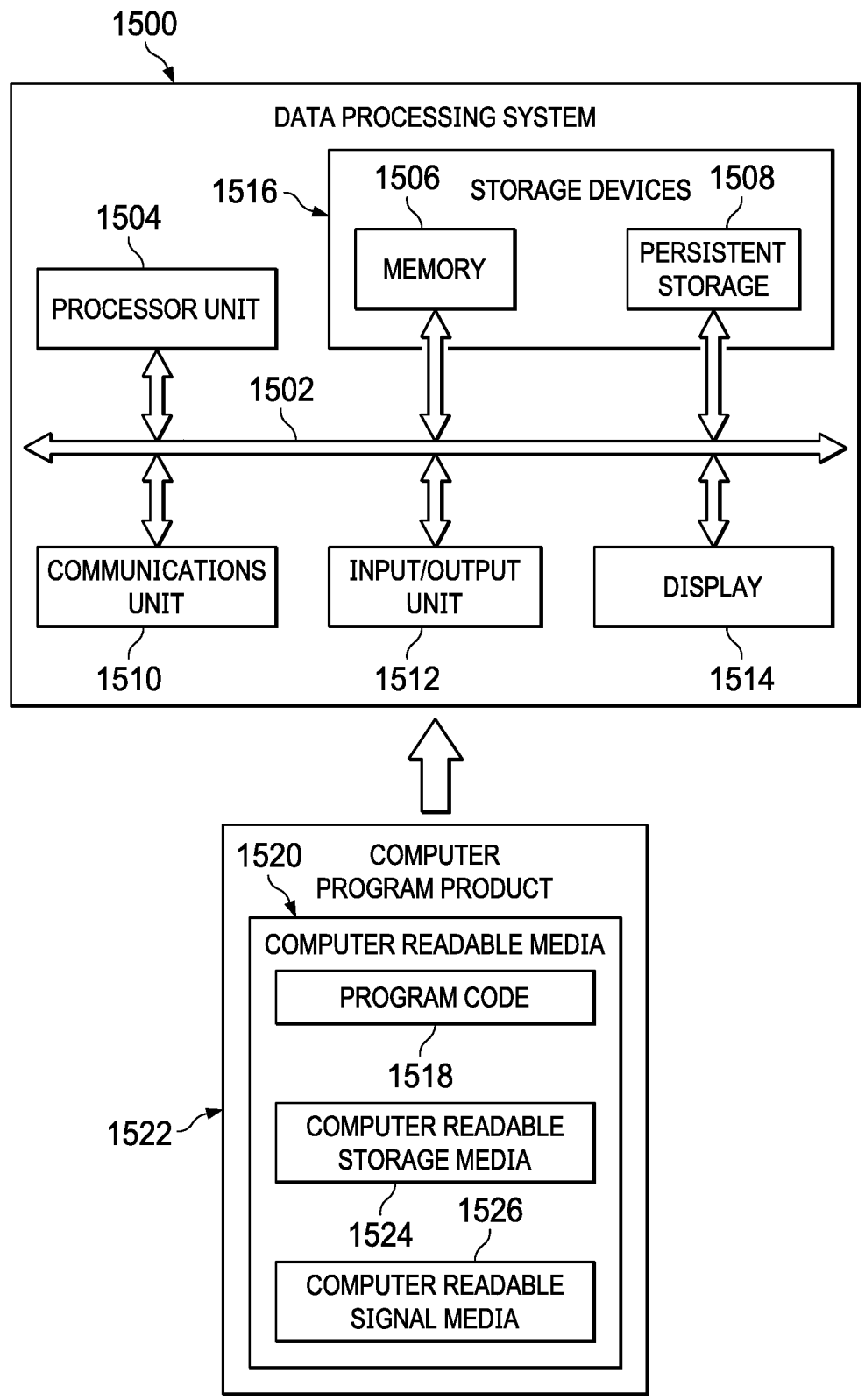
FIG. 15 is an illustration of a block diagram of a data processing system in accordance with an illustrative embodiment.

Turning now to FIG. 15, an illustration of a block diagram of a data processing system is depicted in accordance with an illustrative embodiment. Data processing system 1500 can also be used to implement computer system 122. In this illustrative example, data processing system 1500 includes communications framework 1502, which provides communications between processor unit 1504, memory 1506, persistent storage 1508, communications unit 1510, input/output (I/O) unit 1512, and display 1514. In this example, communications framework 1502 takes the form of a bus system.

Processor unit 1504 serves to execute instructions for software that can be loaded into memory 1506. Processor unit 1504 includes one or more processors. For example, processor unit 1504 can be selected from at least one of a multicore processor, a central processing unit (CPU), a graphics processing unit (GPU), a physics processing unit (PPU), a digital signal processor (DSP), a network processor, or some other suitable type of processor. Further, processor unit 1504 can may be implemented using one or more heterogeneous processor systems in which a main processor is present with secondary processors on a single chip. As another illustrative example, processor unit 1504 can be a symmetric multi-processor system containing multiple processors of the same type on a single chip.

Memory 1506 and persistent storage 1508 are examples of storage devices 1516. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1516 may also be referred to as computer-readable storage devices in these illustrative examples. Memory 1506, in these examples, can be, for example, a random-access memory or any other suitable volatile or non-volatile storage device. Persistent storage 1508 can take various forms, depending on the particular implementation.

For example, persistent storage 1508 may contain one or more components or devices. For example, persistent storage 1508 can be a hard drive, a solid-state drive (SSD), a flash memory, a rewritable optical disk, a rewritable magnetic tape, or some combination of the above. The media used by persistent storage 1508 also can be removable. For example, a removable hard drive can be used for persistent storage 1508.

Communications unit 1510, in these illustrative examples, provides for communications with other data processing systems or devices. In these illustrative examples, communications unit 1510 is a network interface card.

Input/output unit 1512 allows for input and output of data with other devices that can be connected to data processing system 1500. For example, input/output unit 1512 can provide a connection for user input through at least one of a keyboard, a mouse, or some other suitable input device. Further, input/output unit 1512 can send output to a printer. Display 1514 provides a mechanism to display information to a user.

Instructions for at least one of the operating system, applications, or programs can be located in storage devices 1516, which are in communication with processor unit 1504 through communications framework 1502. The processes of the different embodiments can be performed by processor unit 1504 using computer-implemented instructions, which can be located in a memory, such as memory 1506.

These instructions are referred to as program code, computer usable program code, or computer-readable program code that can be read and executed by a processor in processor unit 1504. The program code in the different embodiments can be embodied on different physical or computer-readable storage media, such as memory 1506 or persistent storage 1508.

Program code 1518 is located in a functional form on computer-readable media 1520 that is selectively removable and can be loaded onto or transferred to data processing system 1500 for execution by processor unit 1504. Program code 1518 and computer-readable media 1520 form computer program product 1522 in these illustrative examples. In the illustrative example, computer-readable media 1520 is computer-readable storage media 1524.

Computer-readable storage media 1524 is a physical or tangible storage device used to store program code 1518 rather than a media that propagates or transmits program code 1518. Computer-readable storage media 1524, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Alternatively, program code 1518 can be transferred to data processing system 1500 using a computer-readable signal media. The computer-readable signal media are signals and can be, for example, a propagated data signal containing program code 1518. For example, the computer-readable signal media can be at least one of an electromagnetic signal, an optical signal, or any other suitable type of signal. These signals can be transmitted over connections, such as wireless connections, optical fiber cable, coaxial cable, a wire, or any other suitable type of connection.

Further, as used herein, "computer-readable media 1520" can be singular or plural. For example, program code 1518 can be located in computer-readable media 1520 in the form of a single storage device or system. In another example, program code 1518 can be located in computer-readable media 1520 that is distributed in multiple data processing systems. In other words, some instructions in program code 1518 can be located in one data processing system while other instructions in program code 1518 can be located in one data processing system. For example, a portion of program code 1518 can be located in computer-readable media 1520 in a server computer while another portion of program code 1518 can be located in computer-readable media 1520 located in a set of client computers.

The different components illustrated for data processing system 1500 are not meant to provide architectural limitations to the manner in which different embodiments can be implemented. In some illustrative examples, one or more of the components may be incorporated in or otherwise form a portion of, another component. For example, memory 1506, or portions thereof, can be incorporated in processor unit 1504 in some illustrative examples. The different illustrative embodiments can be implemented in a data processing system including components in addition to or in place of those illustrated for data processing system 1500. Other components shown in FIG. 15 can be varied from the illustrative examples shown. The different embodiments can be implemented using any hardware device or system capable of running program code 1518.

Figure 16:
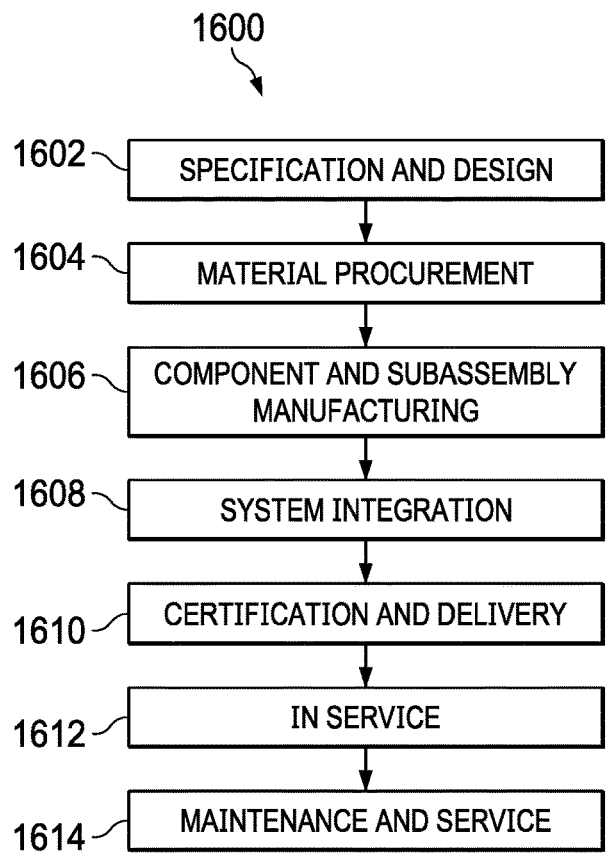
FIG. 16 is an illustration of an aircraft manufacturing and service method in accordance with an illustrative embodiment.
Figure 17:
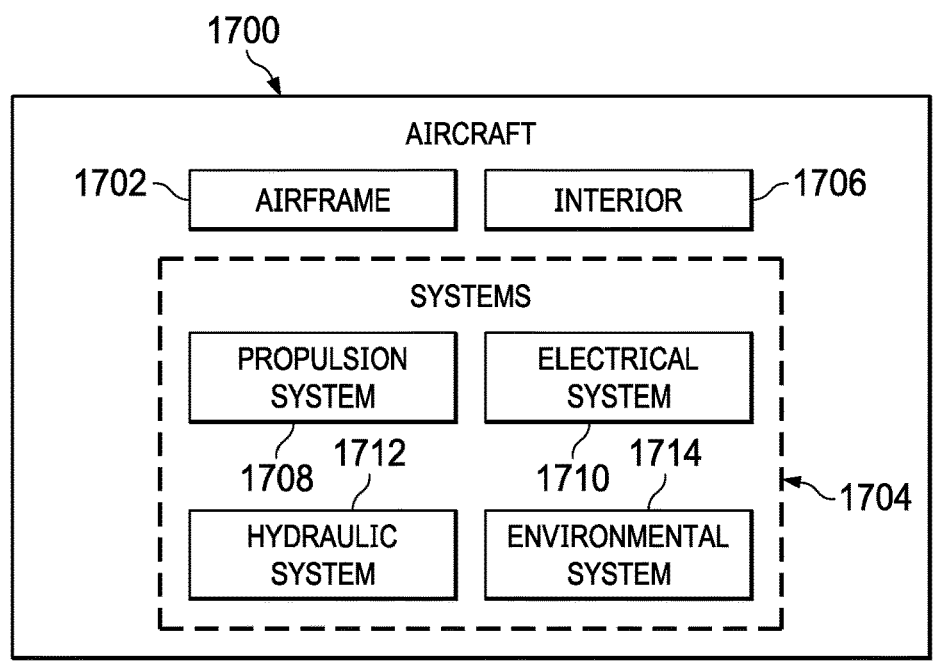
FIG. 17 is an illustration of a block diagram of an aircraft in which an illustrative embodiment may be implemented.

Illustrative embodiments of the disclosure may be described in the context of aircraft manufacturing and service method 1600 as shown in FIG. 16 and aircraft 1700 as shown in FIG. 17. Turning first to FIG. 16, an illustration of an aircraft manufacturing and service method is depicted in accordance with an illustrative embodiment. During preproduction, aircraft manufacturing and service method 1600 may include specification and design 1602 of aircraft 1700 in FIG. 17 and material procurement 1604.

During production, component and subassembly manufacturing 1606 and system integration 1608 of aircraft 1700 in FIG. 17 takes place. Thereafter, aircraft 1700 in FIG. 17 can go through certification and delivery 1610 in order to be placed in service 1612. While in service 1612 by a customer, aircraft 1700 in FIG. 17 is scheduled for routine maintenance and service 1614, which may include modification, reconfiguration, refurbishment, and other maintenance or service.

Each of the processes of aircraft manufacturing and service method 1600 may be performed or carried out by a system integrator, a third party, an operator, or some combination thereof. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 17, an illustration of an aircraft is depicted in which an illustrative embodiment may be implemented. In this example, aircraft 1700 is produced by aircraft manufacturing and service method 1600 in FIG. 16 and may include airframe 1702 with plurality of systems 1704 and interior 1706. Examples of systems 1704 include one or more of propulsion system 1708, electrical system 1710, hydraulic system 1712, and environmental system 1714. Any number of other systems may be included. Although an aerospace example is shown, different illustrative embodiments may be applied to other industries, such as the automotive industry. In this illustrative example, an air monitoring system, such as air monitoring system 104 in FIG. 1, can be implemented in environmental system 1714 and aircraft 1700.

Apparatuses and methods embodied herein may be employed during at least one of the stages of aircraft manufacturing and service method 1600 in FIG. 16.

In one illustrative example, components or subassemblies produced in component and subassembly manufacturing 1606 in FIG. 16 can be fabricated or manufactured in a manner similar to components or subassemblies produced while aircraft 1700 is in service 1612 in FIG. 16. As yet another example, one or more apparatus embodiments, method embodiments, or a combination thereof can be utilized during production stages, such as component and subassembly manufacturing 1606 and system integration 1608 in FIG. 16. One or more apparatus embodiments, method embodiments, or a combination thereof may be utilized while aircraft 1700 is in service 1612, during maintenance and service 1614 in FIG. 16, or both. The use of a number of the different illustrative embodiments may substantially expedite the assembly of aircraft 1700, reduce the cost of aircraft 1700, or both expedite the assembly of aircraft 1700 and reduce the cost of aircraft 1700.

For example, components for an air monitoring system, such as air monitoring system 104, can be designed during specification and design 1602 and manufactured during component and subassembly manufacturing 1606. These components can be installed during system integration 1608 of aircraft 1700. As another example, the different components can be manufactured and installed during maintenance and service 1614. Maintenance and service 1614 can include modification, reconfiguration, refurbishment, and other maintenance or service of aircraft 1700.

The air monitoring system can be operated during operation of aircraft 1700. This air monitoring system can collect data for analysis in updates or changes in the design of aircraft 1700. For example, these design changes can include at least at least one of selecting insulation blankets, stringer layouts, or other components that may be located between the insulation layer and the skin of aircraft 1700.

In another example, the air monitoring system can operate during in service 1612 to monitor for air quality in the cabin, flight deck, galley, laboratories, cargo area, or other areas within aircraft 1700. This operation can be used to monitor air quality during the flight of aircraft 1700.

Thus, the illustrative examples provide a method, apparatus, system, and computer program product for an air monitoring system. In one illustrative example, a method for monitoring air is provided. Air is moved from a collection port connected to a tube as diverted air. The diverted air is moved from the tube thorough an input port in an air interface, through a chamber in the air interface, and out of a pump port in the air interface without increasing a pressure of the diverted air greater than a pressure level for the gas analyzer system to analyze an air sample collected from the diverted air during movement of the diverted air though the chamber in the air interface. A first airtight seal is present between the tube and the input port and a second airtight seal is present between a probe of the gas analyzer system and a sampling port of the air interface. The air sample is obtained from the diverted air as the diverted air moves using the probe inserted through the sampling port in the air interface as the diverted air moves through the chamber in the air interface. The gas analyzer system analyzes the air sample to determine a set of components in the air sample.

Another embodiment of the present disclosure provides an air monitoring system comprising a computer system and a controller in the computer system. The controller operates to control a pump system to move air from a collection port for a cavity as diverted air to a tube connected to the collection port, move the diverted air into an input port of an air interface connected to the tube, through a chamber in the air interface, and out of a pump port of the air interface without increasing a pressure of the diverted air greater than a pressure level for a gas analyzer system to analyze an air sample collected from the diverted air. The collection port is at a location in the cavity in a platform, wherein an airtight seal is present between the tube and the input port. The controller operates to control the gas analyzer system connected to a sampling port in the air interface by a probe to obtain the air sample from the diverted air moving through the air interface and analyze the air sample to determine a set of components in the air sample.

In the illustrative example, the use of the air interface can be used to draw air from cavities to monitor airflow patterns within the cavities in a platform such as aircraft. Further, the air interface can also be used to draw air from cavities to monitor the air quality at different locations in the platform. In the illustrative example, the air interface can be connected to a valve system that can selectively connect the air interface to multiple collection ports at different locations in one or more cavities.

Further, an air monitoring system in the illustrative example can overcome an issue with real-time monitoring of air quality in an aircraft using a portable gas analyzer such as a portable gas chromatography mass spectrometry (GC-MS) unit. The use of an air interface with a tube network connected to the collection ports in different locations in an aircraft allows for continuously monitoring of air for air quality and variations in real-time without the distance and access limitations of a portable gas chromatography mass spectrometry unit.

The air monitoring system in the illustrative examples overcomes an issue with real-time monitoring of air quality in an aircraft using a portable gas analyzer such as a portable gas chromatography mass spectrometry (GC-MS) unit. The use of interface with a tube network connected to collection ports at different locations in an aircraft allows for continuously monitoring of air samples for air quality and variations in real-time without the distance and access limitations of a portable gas chromatography mass spectrometry (GC-MS) unit.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component can be configured to perform the action or operation described. For example, the component can have a configuration or design for a structure that provides the component an ability to perform the action or operation that is described in the illustrative examples as being performed by the component. Further, to the extent that terms "includes", "including", "has", "contains", and variants thereof are used herein, such terms are intended to be inclusive in a manner similar to the term "comprises" as an open transition word without precluding any additional or other elements.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An air monitoring system comprising:
a computer system; and
a controller in the computer system, wherein the controller operates to:
control a pump system to continuously move air from a collection port for a cavity as diverted air to a tube connected to the collection port, continuously move the diverted air into an input port of an air interface connected to the tube, through a chamber in the air interface, and out of a pump port of the air interface, wherein the collection port is at a location in the cavity in a platform, and wherein an airtight seal is present between the tube and the input port; and
control a gas analyzer system connected to a sampling port in the air interface by a probe to obtain an air sample with the probe from the diverted air in the tube prior to the continuously moving diverted air reaching the chamber of the air interface and analyze the air sample to determine a set of components in the air sample, wherein the probe extends through the sampling port, through the chamber in the air interface located between the sampling port and the input port, and into the input port.

2. The air monitoring system of claim 1, wherein the tube is connected to the collection port by a tube network, and wherein the controller operates to:
control the tube network to draw the air from the collection port at the location in the cavity in the platform as the diverted air to the tube through the tube network in the platform.

3. The air monitoring system of claim 2, wherein the tube network comprises:
network tubes connected to collection ports at locations in a set of cavities in the platform; and
a valve system, wherein the valve system is controlled by the controller to select the collection port such that the pump system operates to continuously move the diverted air from the collection port to the tube and through the air interface.

4. The air monitoring system of claim 1, wherein a gas is injected into a set of cavities in a first location in the set of cavities; the location is a second location in the set of cavities in the platform; wherein in analyzing the air sample to determine the set of components in the air sample, the controller operates to control the gas analyzer system to:
detect the gas in the air sample in the diverted air from the second location in the cavity in the set of cavities through the tube connected to a tube network that is in communication with the collection port in the second location in the cavity in the set of cavities; and
wherein the controller operates to:
determine a velocity of an air flow based on a distance from the first location to the second location, a first time when the gas is injected into the set of cavities at the first location, and a second time when the gas is detected in the air sample from the diverted air in the second location.

5. The air monitoring system of claim 1, wherein the controller operates to determine an air quality of the air at the location in the cavity using an analysis of the air sample generated by the gas analyzer system analyzing the air sample.

6. The air monitoring system of claim 5, wherein the controller determines the air quality of the air at the location in the cavity using the analysis of the air sample generated by the gas analyzer system analyzing the air sample during operation of the platform.

7. The air monitoring system of claim 1, wherein the air interface has a T-shape and the tube has a first diameter that is larger than a second diameter for the probe, and wherein the probe extends into the tube connected to the input port.

8. The air monitoring system of claim 1, wherein the platform comprises one or more of a mobile platform, a stationary platform, a land-based structure, an aquatic-based structure, a space-based structure, an aircraft, a commercial aircraft, a rotorcraft, a tilt-rotor aircraft, a tilt wing aircraft, a vertical takeoff and landing aircraft, a surface ship, a cruise ship, a tank, a personnel carrier, a train, a spacecraft, a space station, a satellite, a submarine, an automobile, a power plant, a bridge, a dam, a house, a manufacturing facility, and a building.

9. A method for monitoring air, the method comprising:
moving air from a collection port connected to a tube as diverted air;
continuously moving the diverted air from the tube thorough an input port in an air interface, through a chamber in the air interface, and out of a pump port in the air interface, wherein a first airtight seal is present between the tube and the input port and a second airtight seal is present between a probe of the gas analyzer system and a sampling port of the air interface, wherein the probe extends through the sampling port, through the chamber located between the sampling port and the input port, and into the input port;
obtaining an air sample from the diverted air in the tube prior to the continuously moving diverted air reaching the chamber using the probe extended through the sampling port in the air interface; and
analyzing, by the gas analyzer system, the air sample to determine a set of components in the air sample.

10. The method of claim 9, wherein the collection port is at a location in a cavity in a platform, and wherein the tube is connected to the collection port by a tube network in the platform and further comprising:
moving the diverted air from the collection port at the location in the cavity in the platform to the tube through the tube network in the platform.

11. The method of claim 10, wherein a gas is injected into a set of cavities in a first location in the set of cavities; the location is a second location in the set of cavities in a platform, and wherein analyzing the air sample to determine the set of components in the air sample comprises:
detecting the gas in the air sample in the diverted air received from the second location in a cavity in the set of cavities through the tube connected to a tube network that is in communication with the collection port in the second location in the cavity in the set of cavities; and further comprising:
determining a velocity of an air flow of the air based on a distance from the first location to the second location and a first time when the gas is injected into the set of cavities at the first location and a second time when the gas is detected in the air sample from the diverted air in the second location.

12. The method of claim 9 further comprising:
determining an air quality of the air at a location of the collection port in a cavity in a platform using an analysis of the air sample generated by the gas analyzer system analyzing the air sample.

13. The method of claim 12, wherein determining the air quality of the air at the location in the cavity using the analysis of the air sample generated by the gas analyzer system analyzing the air sample comprises:
   determining the air quality of the air at the location in the cavity using the analysis of the air sample generated by the gas analyzer system analyzing the air sample during operation of the platform.

14. The method of claim 9, wherein a pressure of both the diverted air and the air sample is at an ambient atmospheric pressure.

15. The air monitoring system of claim 1, wherein a pressure of both the diverted air and the air sample is at an ambient atmospheric pressure.

16. The air monitoring system of claim 1, wherein the gas analyzer system comprises a gas chromatography mass spectrometer.

17. The method of claim 9, wherein the gas analyzer system comprises a gas chromatography mass spectrometer.

18. The air monitoring system of claim 1, wherein the collection port is one of a plurality of collection ports.

19. The air monitoring system of claim 18, wherein the tube is one of a plurality of tubes.

20. The method of claim 9, wherein the collection port is one of a plurality of collection ports.

21. The method of claim 20, wherein the tube is one of a plurality of tubes.

\* \* \* \* \*

UNITED STATES PATENT AND TRADEMARK OFFICE
CERTIFICATE OF CORRECTION

| | | |
|---|---|---|
| PATENT NO. | : 12,163,875 B2 | Page 1 of 1 |
| APPLICATION NO. | : 17/647212 | |
| DATED | : December 10, 2024 | |
| INVENTOR(S) | : Joseph M. Baratto and Ryan B. Wilson | |

It is certified that error appears in the above-identified patent and that said Letters Patent is hereby corrected as shown below:

In the Claims

Column 22, Lines 23-24, correct "the tube thorough an input port" to -- the tube through an input port --

Signed and Sealed this
Twenty-fifth Day of February, 2025

Coke Morgan Stewart
*Acting Director of the United States Patent and Trademark Office*